United States Patent [19]

Pugliese

[11] 4,071,020
[45] Jan. 31, 1978

[54] APPARATUS AND METHODS FOR PERFORMING IN-VIVO MEASUREMENTS OF ENZYME ACTIVITY

[75] Inventor: Peter Pugliese, Bernville, Pa.

[73] Assignee: Xienta, Inc., Bernville, Pa.

[21] Appl. No.: 692,511

[22] Filed: June 3, 1976

[51] Int. Cl.$^2$ .................. A61B 5/00; A61B 10/00; G01N 33/16; G01T 1/161
[52] U.S. Cl. .................. 128/2 A; 23/253 TP; 195/103.5 R; 424/9
[58] Field of Search .......... 128/2 A, 2 E, 2 W, 2.1 E; 195/103.5 R, 103.5 C; 424/7, 9; 23/253 TP

[56] References Cited

U.S. PATENT DOCUMENTS

| 3,388,044 | 6/1968 | Babson | 424/7 |
|---|---|---|---|
| 3,472,738 | 10/1969 | Foster | 128/2 W |
| 3,591,480 | 7/1971 | Neff et al. | 195/103.5 C |
| 3,635,213 | 1/1972 | LaHay | 128/2.1 E |
| 3,659,586 | 5/1972 | Johns et al. | 128/2 E |
| 3,778,350 | 12/1973 | Bergmeyer et al. | 195/103.5 C |
| 3,788,950 | 1/1974 | Hicks et al. | 195/103.5 R |
| 3,911,901 | 10/1975 | Niedrach et al. | 128/2 E |

Primary Examiner—Benjamin R. Padgett
Assistant Examiner—Christine M. Nucker
Attorney, Agent, or Firm—Gottlieb, Rackman & Reisman

[57] ABSTRACT

There are disclosed apparatus and methods for performing in-vivo measurements of enzyme kinetics on the epidermis and mucous membranes of a subject. One or more reactants are placed on a predetermined area of the skin in order to react with the enzyme or other biological substance of interest. At least one physical characteristic of one or more of the reaction products formed is measured. Changes in enzymatic or related activity in response to various stimuli can be observed by continuously monitoring the physical characteristic of the reaction product while certain controls are varied, thereby providing dynamic information not previously obtainable.

17 Claims, 6 Drawing Figures

APPARATUS AND METHODS FOR PERFORMING IN-VIVO MEASUREMENTS OF ENZYME ACTIVITY

This invention relates to apparatus and methods for performing measurements of enzyme activity, and more particularly, to in-vivo measurements of enzyme kinetics on the intact skin (within and on the epidermis) of any accessible body surface of a patient.

Medical researchers have long recognized that the rates of reaction of enzymes and other enzyme-related chemicals in the epidermis and mucous membranes, when measured, provide important medical information. This information may relate to various abnormal dermatological conditions, or it may be useful in determining the effect of various ingested or topically applied substances on the metabolic pathways of the normal epidermis. In addition, certain information about the bloodstream may be determined by quantitating the related epidermal enzymatic activity.

In the prior art, the traditional approach in the study of enzyme kinetics has been to remove a skin sample of predetermined quantity from the subject and to form from it a cell suspension. Standard techniques for removing skin specimens include scraping, cutting, blister formation, stripping and suction. Typically, the study of the enzymes of the pentose phosphate pathway has involved subsequent insertion of the cell suspension in a fluorometer cell, and irradiation of the suspension by ultra-violet light of a predetermined wavelength. When the substrate corresponding to the enzyme of interest and a co-factor are added to the suspension, one or more reaction products are formed, and these reaction products fluoresce at known wavelengths. A comparison of the intensity of the fluorescence with statistical norms allows the quantities of the reaction products to be determined, and the amount of the related enzyme which was present in the original cell suspension can be calculated therefrom. Thus, a considerable amount of information concerning the health of the patient can be obtained and recorded for further study.

The basis for the prior art in-vitro measurement techniques is that a known quantity of cells is placed in suspension. It is only in this way that the intensity of the fluorescence can be compared with the intensity expected from a "normal" skin sample. It would be highly desirable to be capable of performing such a test directly on the intact skin of a patient. The test procedure would in such a case be far less time-consuming and cheaper, and the results would be immediate. Moreover, such an in-vivo measurement technique would permit normal physiological parameters to act on the particular enzyme system being studied, thereby providing dynamic physiological information not obtainable using prior art in-vitro measurement methods. In-vivo testing on the skin of a patient, however, has been limited in the past to the measurement of such factors as skin resistance, which is a function of the moisture content of the skin, and the pressure of carbon dioxide in the bloodstream, which is a function of the pressure of carbon dioxide within the tissues of the skin. The latter technique has been described in U.S. Pat. No. 3,659,586. But the prior art has failed to provide a way in which to measure enzyme or other enzyme-related chemical activity directly on the skin or mucous membranes of a patient.

It is therefore a general object of my invention to provide apparatus and methods for performing in-vivo measurements of enzyme and other chemical activity on the skin and mucous membranes of a patient.

I have discovered that by applying a reagent to the skin or mucous membranes of a patient to react with the enzyme or other chemical of interest, the resulting reaction product can be measured directly, and the observed measurements parallel those obtained with conventional in-vitro measurement techniques. It is essential in performing an in-vivo measurement in accordance with my invention that a predetermined area of the skin or mucous membrane be designated and operated upon; this localization of area, common to all measurements, is the common denominator which allows the measurements to be correlated with each other. In the illustrative embodiment of my invention, a skin enzyme is quantitated by applying a conventional substrate and co-factor to a predetermined area of the skin, thereby effecting the same kind of reaction previously utilized in the prior art in-vitro cell suspensions; thereafter, the skin is irradiated with ultraviolet light, and the intensity of the resulting fluorescence is measured. The measurement is compared with the statistical norm to determine the medical information of interest. The fact that accurate in-vivo measurements of this type can be obtained, can be verified by comparing the results of in-vivo measurements with the results obtained by use of conventional in-vitro measurement techniques. Naturally, the quantitative results of the measurements are different because the test procedures are different in the two cases. However, the test results in both cases, when compared with the statistical norms in both cases, are the same, thus verifying that in-vivo measurements indeed produce accurate results.

The techniques of my invention are generally applicable to the testing of enzyme and other biochemical activity. For example, the placement of a substrate and co-factor on the skin of a patient for reacting with a particular enzyme may result in a reaction product, one of whose physical characteristics when measured provides an indication of the quantity of enzyme present on the skin area being operated upon. On the other hand, it may be an enzyme that is applied to the patient's skin in order to measure the quantity of substrate present; in such a case, the measurement of a physical characteristic of a reaction product of the enzyme and substrate provides a measure of the quantity of substrate present in the localized area.

The techniques of the invention are not limited solely to medical applications. For example, there is a very great need in the cosmetic industry to study the effects of various base ingredients and formulations on epidermal metabolism. The techniques of my invention allow in-vivo measurement and monitoring of the effects of these substances by recording the activity of the epidermal enzymes of interest directly on the skin after the cosmetic agent has been applied.

As an investigative tool, the techniques of my inventions are without equal. As will be described in detail below, the in-vivo measurement of enzyme or other biochemical activity permits continuous recording as various controls are changed. Some of the experimental results thus far obtained will be described below. At this point, suffice it to say that as a result of the in-vivo continuous recording of certain measurements, completely unexpected results have been found, which results may lead to a greater understanding of the underlying metabolic pathways.

In the illustrative embodiment of my invention, the physical characteristic of the reaction product which is measured is its fluorescence at a particular wavelength when irradiated at another particular wavelength. But it is to be understood that many different techniques can be used to measure a physical characteristic, among these spectrophotometric, fluorometric, colorimetric and electronic techniques. (For example, the extent of the absorption or the reflection of a particular wavelength of light may be a function of the quantity of reaction product formed on the skin surface.) In all cases, the underlying principle which validates the measurements is that the quantitative measurement on the skin or mucous membranes of a given patient bears the same relationship to the "normal" measurement under the same conditions as the conventional in-vitro measurement performed on a skin sample of the same patient bears to the "normal" in-vitro measurement.

Further objects, features and advantages of my invention will become apparent upon consideration of the following description in conjunction with the drawings, in which.

Figure 1:
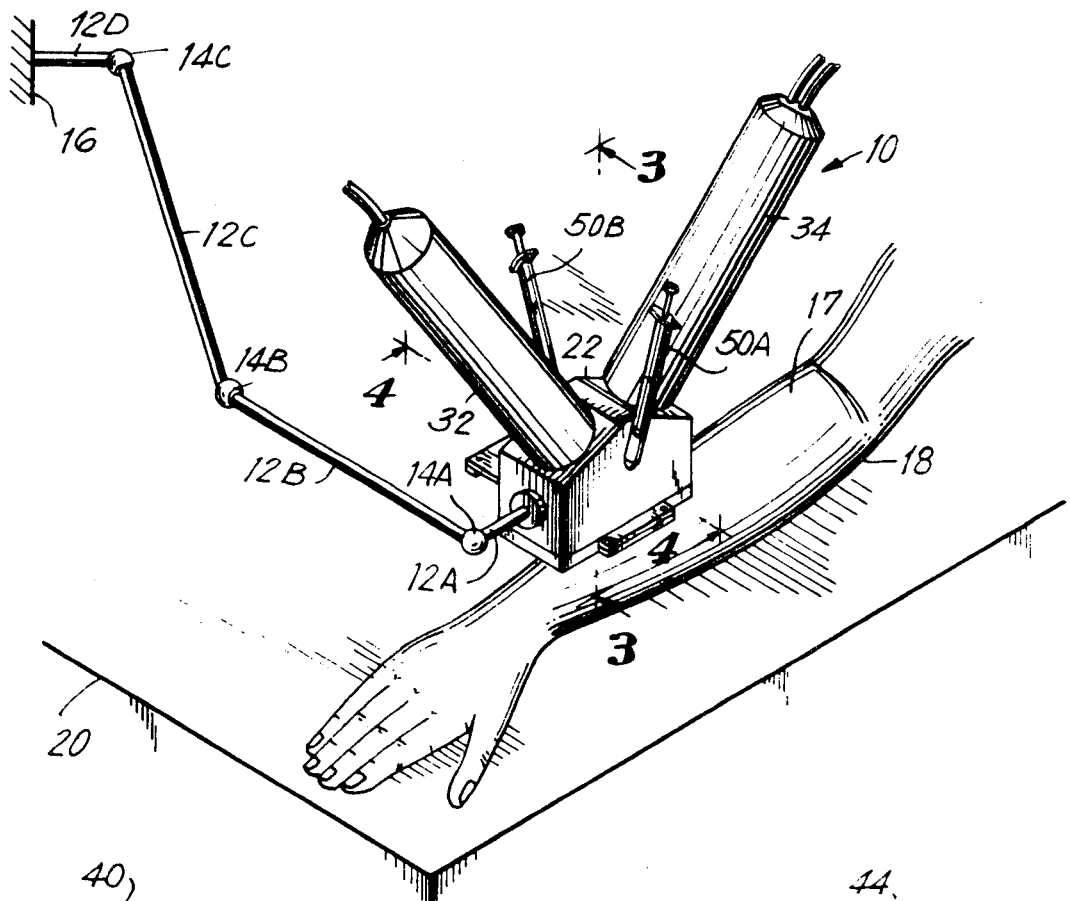
FIG. 1 is a perspective partial view of an apparatus constructed in accordance with the principles of my invention, showing the apparatus positioned on the arm of a subject for direct measurement of enzymatic activity.

Referring to the drawings, and specifically to FIG. 1, the apparatus for conducting in-vivo enzymatic determinations is generally designated by the numeral 10. Apparatus 10 is suspended for omni-directional movement in a conventional manner, such as by struts 12A, 12B, 12C, 12D, which are pivotally interconnected by ball-and-socket joints 14A, 14B, 14C, and which may be secured to a wall 16 in a customary manner. The apparatus may also be hand-held for additional support.

As shown in FIG. 1, apparatus 10 is illustratively positioned immediately adjacent to the dorsal surface 17 of the right arm 18 of the subject. For convenience, arm 18 rests upon and is supported by a flat surface, such as table 20.

Figure 2:
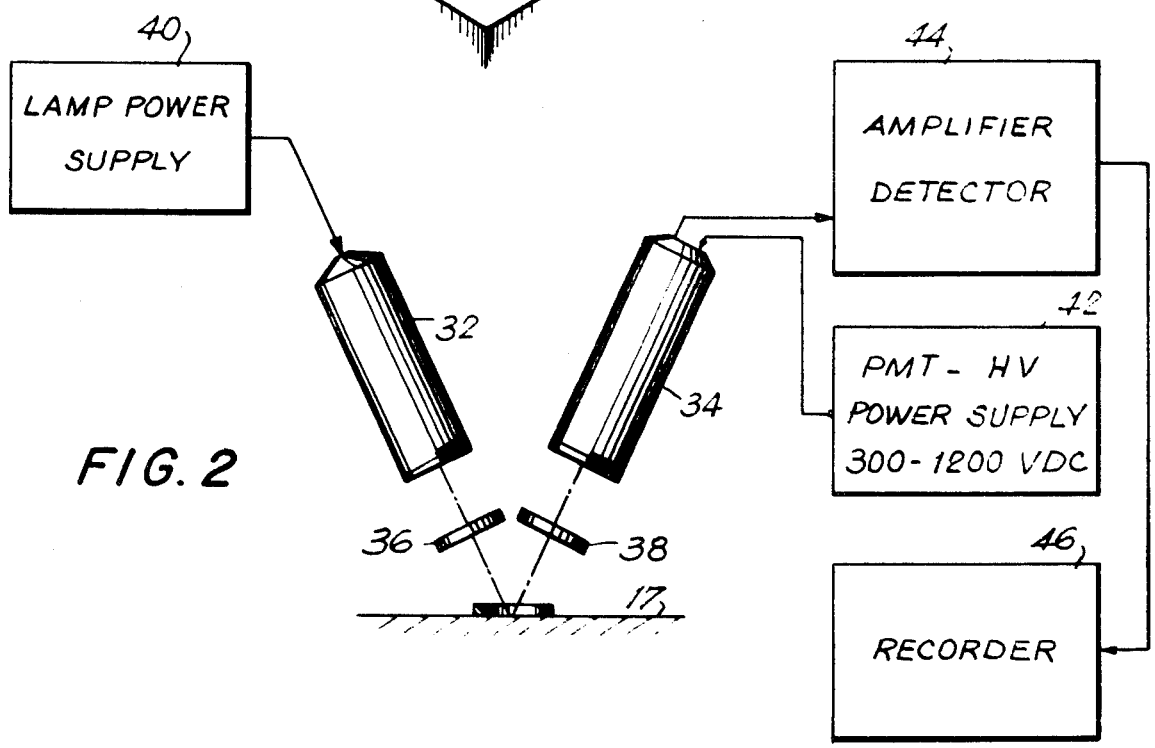
FIG. 2 is a schematic block diagram of the same apparatus, showing additional components of the system.
Figure 3:
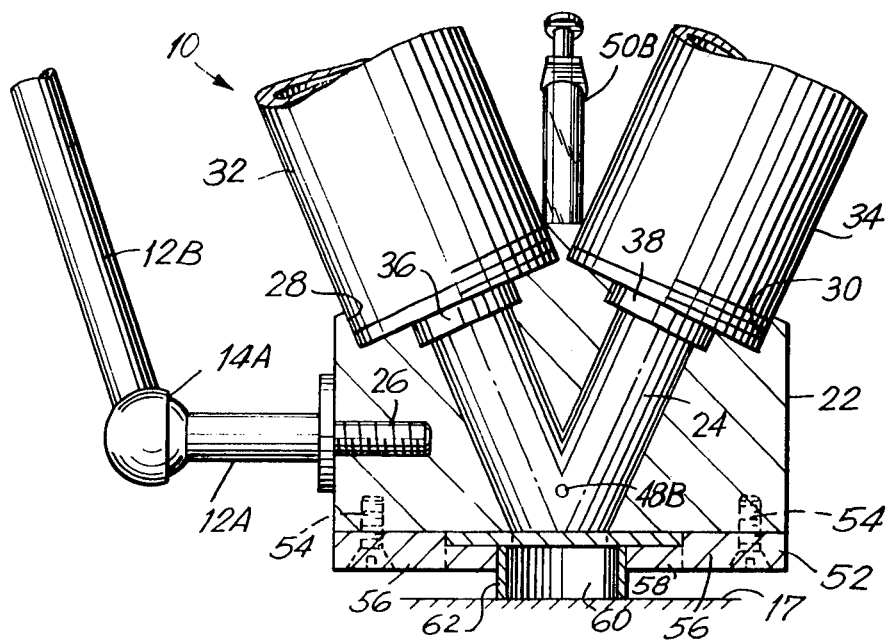
FIG. 3 is a partial sectional view taken along line 3—3 of FIG. 1.
Figure 4:
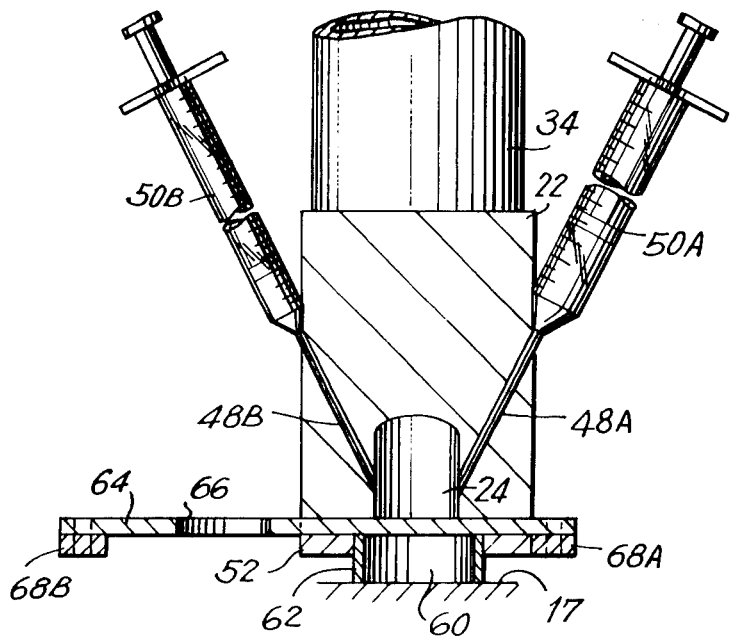
FIG. 4 is a partial sectional view taken along line 4—4 of FIG. 1.

As shown most clearly in FIGS. 2, 3 and 4, in the illustrative embodiment of my invention, apparatus 10 is secured to strut 12A by conventional means, such as bolt 26, and comprises a housing 22 having a chamber 24 defined therein. Chamber 24, which is roughly V-shaped in cross-section (see FIG. 3), is provided at its outer ends with internally threaded apertures 28, 30, adapted to accomodate an ultraviolet light source 32 and a photomultiplier tube 34, both of which are externally threaded for insertion in apertures 28, 30, respectively. Ultraviolet light sources, such as the General Electric GEF4T4 Germicidal UV lamp, are widely available commercially. Similarly, photomultiplier tubes for use herein, such as the Model EMI9524B of EMI GENCOM INC. of Plainview, N.Y. may be readily purchased.

In the preferred embodiment, apertures 28, 30 of housing 22 are machined such that ultraviolet light source 32 and photomultiplier tube 34 are both positioned at an angle with is approximately 22.5° from the vertical when they are inserted in apertures 28, 30, respectively.

Ultraviolet light source 32 is provided with a filter 36, such as the Corning No. 5850 filter or the Wratten 18A Kodak filter. The output of ultraviolet light source 32 which passes through the filter is thereby limited to wavelengths in the range 340 to 365 millimicrons. Similarly, any suitable ultraviolet filter 38, such as the Corning No. 3389 filter or the Kodak UV filter 2B, is positioned at the face of photomultiplier tube 34 to block ultraviolet light; the photomultiplier tube responds to the visible light generated by the fluorescence of the reaction product on the skin (within and on the epidermis) of the patient.

As shown in FIG. 2, ultraviolet light source 32 is powered by a standard power supply, represented by block 40. Block 42 symbolizes a high voltage power supply for the photomultiplier tube 34, such as the Model 6515A DC Power Supply of the Hewlett-Packard Company. Preferably, power supply 42 is capable of generating from 300 to 1200 volts.

The output from photomultiplier tube 34 is coupled to a standard amplifier circuit 44, and the amplified signal is recorded by recorder 46, which may illustratively be a Honeywell Electronik 19, set at a speed of ½ inch per minute.

As shown in FIG. 4 housing 22 is also provided with holes 48A, 48B, each of which is bored at an angle of 22.5° from the vertical. Holes 48A, 48B, are of sufficient diameter to accommodate 22 gauge needles, and provide the means by which reactants may be introduced into chamber 24 using syringes 50A, 50B. Housing 22 also has a plate 52 secured to the underside thereof by screws 54. As shown best in FIG. 3, plate 52 has flanged end-portions 56, and a reduced mid-portion 58 in which a circular aperture 60 is defined by ring 62. When plate 52 is secured to housing 22 as shown in FIG. 3, aperture 60 is positioned immediately adjacent to chamber 24.

Figure 5:
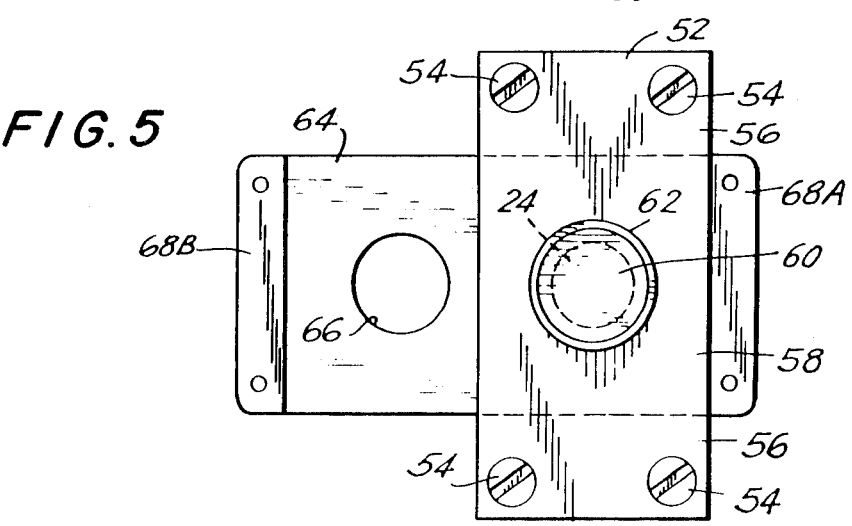
FIG. 5 is a bottom elevation view of the same apparatus.

In order to provide selective communication between chamber 24 and aperture 60, a slide 64 is disposed for reciprocal movement between housing 22 and reduced mid-portion 58 of plate 52. As shown best in FIGS. 4 and 5, slide 64 is provided with a circular aperture 66, and with enlarged end-portions 68A, 68B. End-portions 68A, 68B serve to define and limit the motion of slide 65 so that slide 64 may reciprocate between a closed position, shown in FIGS. 4 and 5, and an open position (not shown) in which aperture 66 is aligned with and permits communication with chamber 24. When slide 64 is in the closed position, in-vitro enzymatic reactions can be conducted to calibrate apparatus 10. Moreover, slide 64, when closed, prevents light from reaching photomultiplier tube 34, thereby permitting apparatus 10 to be adjusted on the subject's skin or moved without damaging photomultiplier tube 34.

Use of apparatus 10 in accordance with the principles of the invention depends upon the particular epidermal biochemical system to be studied, for example, the enzyme system involved with glucose metabolism of the epidermis, and more particularly, the enzymes of the pentose phosphate pathway such as glucose-6-phosphate dehydrogenase, 6-phosphogluconic dehydrogenase, isocitric dehydrogenase, and lactic acid dehydrogenase. It has been reported that these enzymes are involved in such processes as drug detoxification, lipogenesis, and steroid metabolism.

It is well known in the art that the enzymes of the pentose phosphate pathway and their corresponding substrates are nicotinamide adenine dinucleotide phosphate (NADP)-dependent. That is, this co-factor (NADP) reacts with the enzyme and its associated substrate, and is reduced thereby, producing NADPH. The presence of NADPH may be detected, since this compound, in its reduced state only, fluoresces at a wavelength of 460 millimicrons when irradiated at a wavelength of 340–365 millimicrons. Since the amount of light emitted is directly proportional to the amount of the reduced nucleotide which is formed, the amount of enzyme or substrate originally present may be calculated by measuring the intensity of the resulting fluorescence.

Before in-vivo enzyme measurements can be conducted, apparatus 10 must be calibrated in order to insure that the results obtained from different subjects can be compared. First, with slide 64 in its closed position and with ultraviolet light source 32 and photomultiplier tube 34 turned on, a known amount of NADPH is inserted into chamber 24 of apparatus 10 my means of syringe 50A. The intensity of the fluoresence of the NADPH is detected and recorded on recorder 46, and this process is repeated for other known quantities of NADPH until a sensitivity curve is obtained. Because of minute changes in the sensitivity of apparatus 10, this calibration step is preferably repeated on a daily basis.

Further calibration is required each time a new enzyme or other chemical is chosen for study in order to relate the sensitivity curve to the enzyme or other chemical being measured. In the case of glucose-6-phosphate dehydrogenase, this calibration can illustratively be conducted using the following concentrations and quantities of reactants:

| Reactants | Amount |
| --- | --- |
| Glucose-6-phosphate | $5.8 \times 10^{-3}$M, in tris buffer with $MgCl_2$ at pH 7.4 |
| Glucose-6-phosphate dehydrogenase | 0.05 units in distilled water |
| NADP | 0.04 mg/cc |

The co-factor, NADP, is added incrementally by 0.1 cc aliquots (0.004 mg) until a steady-state reaction is obtained (that is, until further addition of NADP does not affect the intensity of the fluorescence of the reaction product, NADPH). Thus, an indication of the intensity of the fluorescence produced by a known quantity of the enzyme to be studied can be obtained.

Chamber 24 is then flushed with distilled water, and an additional aliquot of substrate (glucose-6-phosphate) and co-factor (NADP) is added to insure that no residual enzyme remains within chamber 24. The system, after cleansing again with distilled water, is ready for in-vivo measurements.

The portion of the skin of a patient which has been selected for study is cleansed with distilled water and surgical gauze to remove loose stratum corneum and associated debris. As shown in FIG. 1, apparatus 10 is then placed gently on the skin, using only enough pressure to allow a water-tight and light-tight seal. This is accomplished by positioning apparatus 10 so that ring 62 is directly adjacent to the skin surface 17 and surrounds the site to be studied. (See FIGS. 3 and 4.) No sealant is used.

After the instrument is properly positioned, slide 64 is placed in the open position, and the skin surface 17 is exposed to irradiation from ultraviolet light source 32. At this point, a small amount of fluorescence is detected by photomultipier tube 34 and is recorded on recorder 46. This is due to the native fluorescense of the skin, which is attributable to many components thereof, including a small proportion of reduced nucleotides. This natural skin fluoresence may, however, be discounted when the actual enzymatic determinations are made. The bias of recorder 46 is therefore adjusted to establish a base line level of fluorescence, which is then allowed to stabilize for at least 5 minutes.

The substrate of the enzyme to be studied is then introduced into chamber 24 by means of syringe 50B. Illustratively, approximately 1 to 2 cc of glucose-6-phosphate may be added. Another increase in fluorescence, due to a refractive phenomenon, is then observed, and the skin base line is allowed to stabilize once again. Thereafter, the co-factor, NADP, is added in 0.1 cc increments. If glucose-6-phosphate dehydrogenase is present, NADPH will be generated, and an increase in the intensity of the fluorescence will be observed on recorder 46. Additional increments of the co-factor are added until a steady-state reaction is obtained (i.e., until the addition of NADP causes no change in the intensity of the observed fluorescence.)

Thereafter, various other controls may be changed and the resulting effect on the production of the enzyme being studied can be observed and recorded. For example, relative anoxia can be induced locally in the epidermis by placing a tourniquet on the extremity near the site being studied. The effect of both the anoxic state and of relief of anoxia on the production of glucose-6-phosphate dehydrogenase have been studied in detail, and will be described in connection with FIG. 6.

It will be apparent to those skilled in the art that the illustrative embodiment of the present invention may also be utilized to detect a reduction in fluorescence. For example, if lactic acid dehydrogenase is the enzyme of interest, the co-factor is added in its reduced state (e.g., NADH) and the subsequent reduction in fluorescence as NADH is converted into NAD will indicate the presence of this enzyme.

Figure 6:
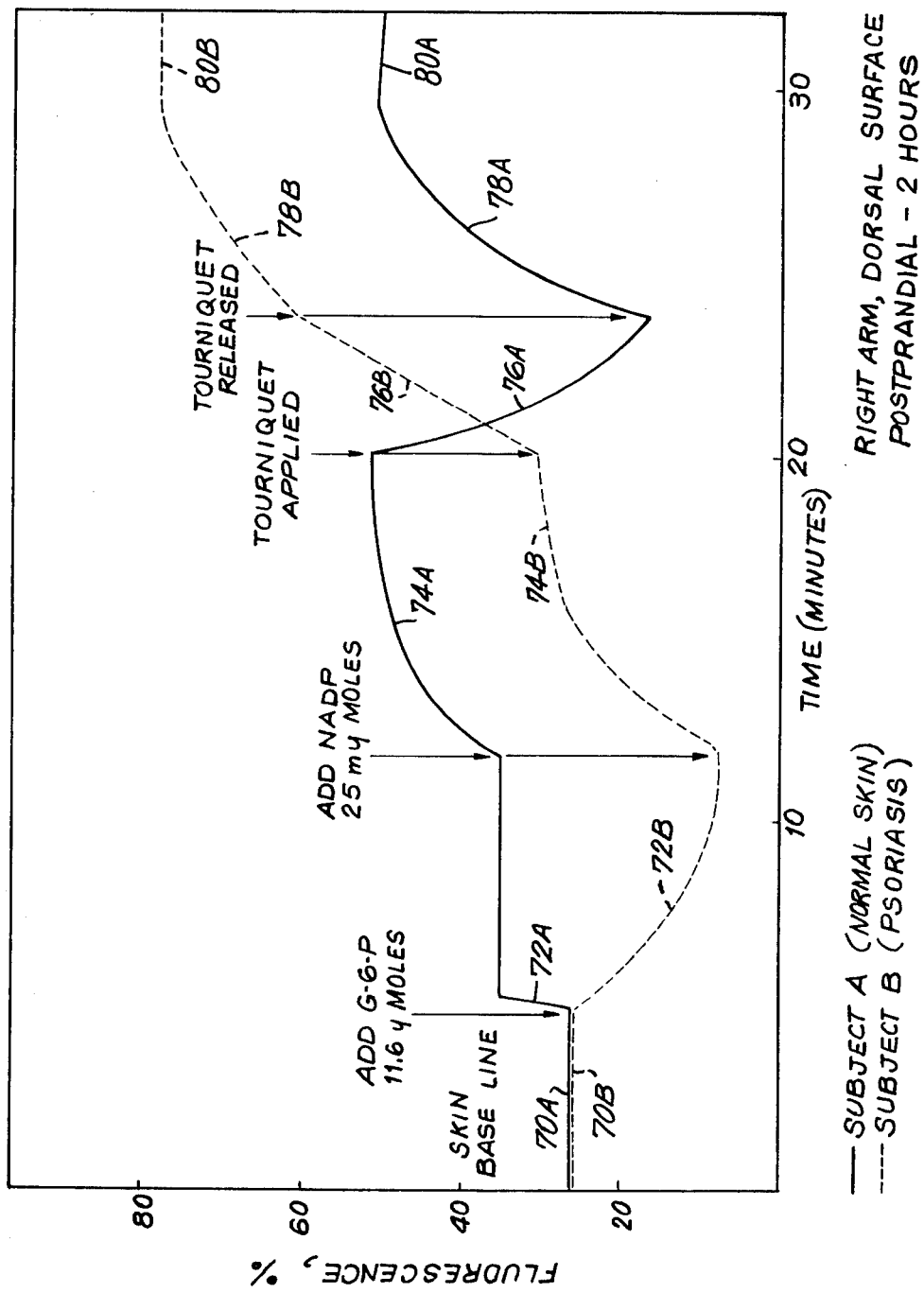
FIG. 6 is a graphic illustration of some experimental results obtained using the apparatus of FIG. 1.

In FIG. 6, the graph shows certain important and heretofore unexpected changes in enzymatic activity which were observed using the illustrative embodiment of the present invention. The solid line depicts the activity of glucose-6-phosphate dehydrogenase in a subject with normal skin, while the dashed line illustrates the comparable activity in a subject with psoriasis. In both cases, the dorsal surface of the right arm of a 2 hour postprandial subject was studied. After the establishment of a skin base line 70A, 70B for each subject, 11.6 micromoles of the substrate glucose-6-phosphate was added. Although the expected increase in fluorescence 72A due to refraction was observed on the normal skin, an unexpected decrease in fluorescence 72B was detected on the psoriatic skin. Upon the addition of 25 millimicromoles of NADP, the expected increase in fluorescence 74A, 74B due to the production of NADPH was observed with both subjects.

After a steady state was achieved, a tourniquet was used to create relative anoxia at the site being studied. The anoxic state caused a sharp decrease in fluorescence 76A in the normal subject indicating, it is believed, a shift from pyruvate to lactate production. Relief of anoxia caused a return 78A to the previous steady-state level 80A for normal skin.

However, in the subject with psoriasis, relative anoxia caused a completely unexpected increase 76B in glucose-6-phosphate dehydrogenase activity, and relief of anoxia caused an additional increase 78B before a steady-state level 80B was achieved. This marked difference in response to anoxia in psoriatic subjects, when compared to normal subjects, is not completely understood, and will require further study of the underlying metabolic pathways.

It has also been found that the activity of glucose-6-phosphate dehydrogenase in normal subjects is related to the degree of fasting. Subjects fasting over four hours produced the lowest reaction rates.

Although the invention has been described with reference to a particular embodiment, it is to be understood that this embodiment is merely illustrative of the application of the principles of the invention. For example, when studying epidermal glucose (the amount of which is proportional to the concentration of glucose in the bloodstream), an electronic technique employing a bioelectrode may be utilized to measure another physical characteristic (namely, the pH) of the reaction product formed when a known amount of the corresponding enzyme, glucose oxidase, is applied to a predetermined area of the skin. Numerous other modifications, such as the provision of a remote sensing device for the particular physical characteristic being measured, may also be utilized without departing from the spirit and scope of the invention.

What I claim is:

1. Apparatus for performing an in-vivo measurement of a substrate, enzyme, or other biochemical agent on the skin or mucous membranes of an accessible body surface of a patient comprising means for reacting at least one chemical with said substrate, enzyme or other biochemical agent on a predetermined area of the skin or mucous membranes of the patient to produce at least one reaction product, and means for measuring a physical characteristic of said at least one reaction product.

2. Apparatus in accordance with claim 1 wherein said measuring means measures said physical characteristic while said at least one reaction product is on the skin or mucous membranes of the patient.

3. Apparatus in accordance with claim 2 wherein said measuring means includes first means for irradiating said at least one reaction product while on the skin or mucous membranes of the patient and second means for measuring a wavelength-dependent physical characteristic thereof.

4. Apparatus in accordance with claim 3 wherein said second means measures the intensity of the fluorescence of said at least one reaction product while it is being irradiated by said first means.

5. Apparatus in accordance with claim 1 wherein said physical characteristic is wavelength-dependent.

6. Apparatus in accordance with claim 5 wherein said measuring means includes first means for irradiating said at least one reaction product and second means for measuring the intensity of the fluorescence of said at least one reaction product while it is being irradiated by said first means.

7. A method for performing an in-vivo measurement of a substrate, enzyme, or other biochemical agent on the skin or mucous membranes of an accessible body surface of a patient comprising the steps of reacting at least one chemical with said substrate, enzyme or other biochemical agent on a predetermined area of the skin or mucous membranes of the patient to produce at least one reaction product, and measuring a physical characteristic of said at least one reaction product.

8. A method in accordance with claim 7 wherein said physical characteristic is measured while said at least one reaction product is on the skin or mucous membranes of the patient.

9. A method in accordance with claim 8 wherein said measuring step includes a first sub-step of irradiating said at least one reaction product while on the skin or mucous membranes of the patient and a second sub-step of measuring a wavelength-dependent physical characteristic thereof.

10. A method in accordance with claim 9 wherein in said second sub-step the intensity of the fluorescence of said at least one reaction product is measured while it is being irradiated.

11. A method in accordance with claim 8 further including the step of recording continuously the measurements taken over an interval of at least several minutes.

12. A method in accordance with claim 7 wherein said physical characteristic is wavelength-dependent.

13. A method in accordance with claim 12 wherein said measuring step includes a first sub-step of irradiating said at least one reaction product and a second sub-step of measuring the intensity of the fluorescence of said at least one reaction product while it is being irradiated.

14. A method in accordance with claim 13 wherein said at least one chemical includes nicotinamide adenine dinucleotide phosphate, and said at least one reaction product includes reduced nicotinamide adenine dinucleotide phosphate, and wherein in said first sub-step said at least one reaction product is irradiated by ultraviolet light at a wavelength in the range 350–365 millimicrons, and in said second sub-step the fluorescence of said at least one reaction product is measured at a wavelength of approximately 460 millimicrons.

15. A method in accordance with claim 14 wherein said at least one chemical also includes glucose-6-phosphate, and said enzyme or other biochemical agent is glucose-6-phosphate dehydrogenase.

16. A method in accordance with claim 14 wherein said at least one chemical also includes glucose-6-phosphate dehydrogenase, and said enzyme or other biochemical agent is glucose-6-phosphate.

17. A method in accordance with claim 7 further including the step of recording continuously the measurements taken over an interval of at least several minutes.

* * * * *